United States Patent [19]

Lee et al.

[11] Patent Number: 4,574,793
[45] Date of Patent: Mar. 11, 1986

[54] STABILIZED, CATALYZED WATER ACTIVATED POLYURETHANE SYSTEMS

[75] Inventors: Kyu-Wang Lee, Danville; Winston L. Hedges, Dublin; Kenneth S. Baron, San Ramon, all of Calif.

[73] Assignee: Hexcel Corporation, San Francisco, Calif.

[21] Appl. No.: 642,773

[22] Filed: Aug. 21, 1984

[51] Int. Cl.$^4$ .............................................. A61F 5/04
[52] U.S. Cl. ...................... 128/90; 252/182; 523/105; 523/109; 524/871; 528/53; 528/59
[58] Field of Search ............................ 128/90; 528/53; 523/109, 111, 105; 252/182; 524/871

[56] References Cited

U.S. PATENT DOCUMENTS

| | | | |
|---|---|---|---|
| 3,074,911 | 1/1963 | Harper | 528/53 |
| 3,645,925 | 2/1972 | Speranza | 528/53 |
| 3,789,045 | 1/1974 | Coury | 528/53 |
| 4,026,875 | 5/1977 | Leu | 528/53 |
| 4,048,107 | 9/1977 | Babiec | 528/53 |
| 4,427,002 | 1/1984 | Baron | 128/92 |
| 4,433,680 | 2/1984 | Yoon | 128/90 |

*Primary Examiner*—C. Warren Ivy
*Attorney, Agent, or Firm*—Oblon, Fisher, Spivak, McClelland & Maier

[57] ABSTRACT

Stabilized, catalyzed polyurethane systems are disclosed which are comprised of a polyurethane prepolymer, a tertiary amine catalyst and a stabilizing agent. To extend shelf life, and lend stability to the composition, the stabilizing agent is comprised of methane sulfonic acid. The stabilizer is suitable for use with most polyurethane systems catalyzed by tertiary amines, and produces longer shelf life or stability with lesser amounts than conventional stabilizers.

In a particular embodiment requiring extended shelf life but quick curing times, a catalyst yielding these qualities is bis(2,6-dimethylmorpholino)diethylether. The catalyst, when incorporated in a polyurethane prepolymer coated on a flexible substrate, can be immersed in water, the material thereafter being wrapped about the portion of the patient's body to be immobilized, and cures rapidly, within about 15 minutes. The catalyst can optionally be combined with a stabilizer, such as methane sulfonic acid. When stored in the absence of moisture, such systems have exceedingly long shelf life.

21 Claims, 2 Drawing Figures

STABILIZED, CATALYZED WATER ACTIVATED POLYURETHANE SYSTEMS

BACKGROUND OF THE INVENTION

1. Field of the Invention

This invention relates to curable polyurethane systems, which are generally comprised of a polyurethane prepolymer, a catalyst, and a stabilizer for the system. The systems may generally be cured, or polymerized, by treatment with water, such as through exposure to moisture in the air or by immersion in water. This invention also relates to specific applications of these systems.

2. Description of the Prior Art

Polyurethanes have long been known as excellent high polymer plastics which, owing to the wide variety of characteristics that can be introduced into the polymer by control of the chemical nature of the systems, has been employed in extremely varied applications. Among applications that may be mentioned are paints and varnishes, coatings, construction and constructional materials, bearings and friction parts, etc. One particular application that has received increased attention in recent years is the use of polyurethane polymers carried on a flexible, pliable or drapeable fabric which may be arranged about a limb or other portion of a patient's body, and thereafter cured to form a cast or splint. This type of material enjoys a large number of advantages over prior art materials such as Plaster of Paris, in that the material is lightweight, water resistant, may be made porous, is X-ray transparent, etc.

One exemplary medical cast or splint or similar orthopedic device is disclosed and claimed in U.S. Pat. No. 4,427,002. The polyurethane system employed therein is comprised of a prepolymer which is the reaction product of an isocyanate and a polyol, together with a catalyst and a stabilizer and an antifoamant. The catalyst is provided to ensure relatively quick curing times upon immersion of the carrier fabric saturated with this system in water, such that the cast "sets", or becomes rigid, in less than about 15 minutes.

The stabilizer is introduced to prevent the catalyst from auto-catalyzing alternative reactions to the polyurethane polymerization. One alternative reaction, is the allophanate reaction which is well known in the art, and together with isocyanate trimerization is primarily responsible for the premature solidification or polymerization of polyurethane systems which are intended to be stored for substantial periods of time prior to use. The use of a catalyst in a polyurethane prepolymer system complicates the problems of storage stability, in that catalyst which catalyze the urethane polymerization reaction also tend to catalyze these alternative reactions. As these reactions proceed in the absence of water, such products generally have no appreciable storage life.

The stabilizer is introduced to the system in order to bind to the catalyst, or prevent the catalyst from catalyzing the undesirable reaction before the system is immersed in water. The water immersion frees the catalyst to activate the polyurethane polymerization, thus resulting in rapid curing. In the above-referenced U.S. Pat. No. 4,427,002, the entire disclosure of which is incorporated-herein-by-reference, the stabilizer is preferably identified as a mineral acid.

Another reference directed to orthopedic casting materials is U.S. Pat. No. 4,411,262. A wide variety of isocyanate/polyol reaction product systems are disclosed therein, and the reference identifies the use of certain catalysts in conjunction with those prepolymers to improve the cure times secured. The reference does not specifically discuss the use of any stabilizer.

Another recent document discussing orthopedic casting materials comprised of a polyurethane prepolymer system-saturated carried material in U.S. Pat. No. 4,433,680. The particular catalyst employed in the reference is dimorpholinodiethylether. The particular discovery leading to that patent was the observation that the catalyst, which had been used in polyurethane systems for some time, gave both extended shelf life (i.e., did not excessively catalyze the side reactions) while, at the same time, gave excellent cure times upon water immersion (sufficiently catalyzed the water-isocyanate, or urethane, reaction). The reference identifies the use of benzoyl chloride as a stabilizing agent. Column 3, lines 59-60.

Despite the above-referenced attempts to provide a catalyzed, stabilized polyurethane prepolymer system, there remains a need to find a stabilizing agent capable of preventing premature polymerization in a broad range of polyurethane applications. Additionally, there continues to be a need for a catalyst and stabilizer system that will provide sufficient polyurethane cure times for the orthopedic applications discussed above, and yet yield good shelf life and stability in excess of the dimorpholinodiethylether previously employed.

SUMMARY OF THE INVENTION

It is an object of this invention to provide stabilized, catalyzed polyurethane prepolymer systems, and the cured products thereof, which show excellent shelf life.

It is another object of this invention to provide a stabilized, catalyzed polyurethane prepolymer system that is suitable for saturation of a carrier material which can subsequently be used as an orthopedic casting or splinting material upon immersion in water, which system and saturated carrier has excellent stability and shelf life.

These objects and others of the invention herein which will become evident in the description below, are achieved through the use of methane sulfonic acid as a stabilizing agent for polyurethane prepolymer systems catalyzed with a tertiary amine catalyst.

One particular application wherein the stabilizing activity is of particular value is in the preparation of an orthopedic cast or splint material. A polyurethane prepolymer is provided with a bis(2,6-dimethylmorpholino)diethylether catalyst. The catalyst is highly selective in favor of the prepolymer/water reaction, yielding even better cure times than those secured in the prior art, while substantially extending shelf life. This shelf life can be even further extended by use of MSA as a stabilizing agent.

DETAILED DESCRIPTION OF THE INVENTION

Figure 1:
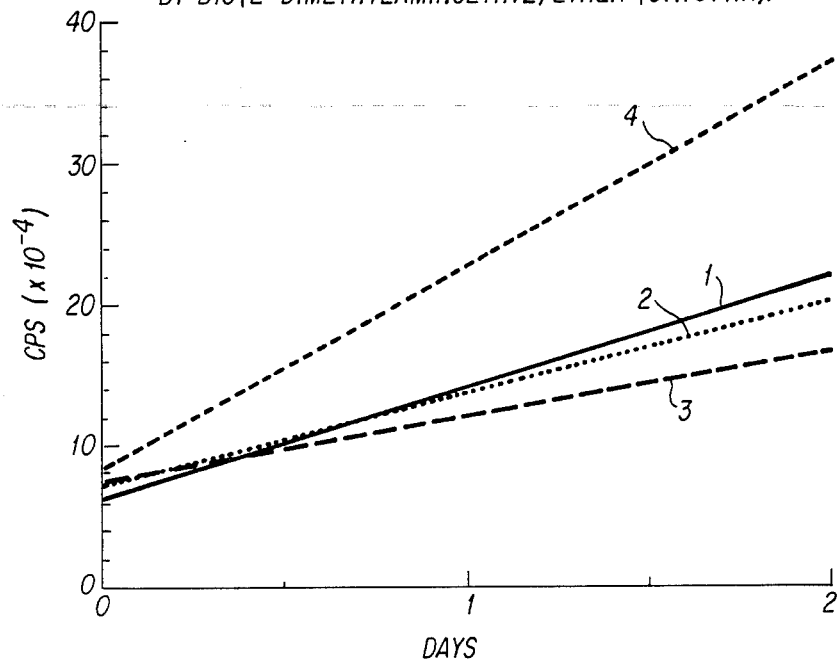
FIG. 1 is a graphic comparison of shelf life and stability of stabilized systems employing a bis(2-dimethylaminoethyl)ether catalyst.

This invention is premised, in part, on the discovery that methane sulfonic acid significantly extends the shelf life, or pre-polymerization stability, of polyurethane systems including tertiary amine catalyst. Although the exact nature of the MSA activity is unknown, it is believed that the stabilizer "complexes" with the tertiary amine, forming a salt-type compound, which is not free to catalyze the side reactions which results in premature polymerization and short shelf life. This complex, or salt, is broken down upon exposure to water, which exposure liberates the tertiary amine catalyst, and frees it to catalyze the prepolymer-water reaction, or urethane polymerization which is desirable. In almost every application where catalyzed prepolymer systems are employed, it is desirable, from a commercial standpoint if no other, to extend the stability, or shelf life, of the system. To the best of Applicants' knowledge, MSA is the best stabilizing agent of broad or universal applicability to tertiary amine catalyzed systems which yields the substantial improvements of shelf life secured herein.

In most applications, the stabilizer should be present in amounts of 0.01-1.0% by weight based on the prepolymer composition. A particularly preferred amount for use in orthopedic casting applications is less than 0.3% by weight, preferably 0.01-0.05% by weight.

Although, as noted, the MSA stabilizer may be added to virtually any polyurethane prepolymer system wherein shelf life or extended stability is desirable, certain specific applications include:

1. Urethane Foams
2. Coatings
3. Moulding
4. Encapsulating and Potting Materials, etc.

In addition to the universal applicability of the MSA as a stabilizer for polyurethane prepolymer system catalyzed with a tertiary amine, the MSA also enjoys other advantages over prior art stabilizers, such as the phosphoric acid and benzoyl chloride mentioned above. In particular, for any given application, much less MSA need be used to secure the same effects as benzoyl chloride. At given levels, the stability achieved through the use of MSA is dramatically improved. These superior qualities of MSA stabilize systems are illustrated by the examples set forth hereinbelow.

The following procedure was used to prepare Prepolymer A:

A 1-liter resin kettle equipped with a thermometer, a mechanical stirrer and nitrogen blanketing was charged with 366.6 grams of 143-L (a diisocyanate available from Upjohn, NCO equivalent 143.5 and based primarily on diphenylmethane diisocyanate with polycarbodiimide adducts); 244.2 grams of P-1010 (a polyether diol available from BASF, having a OH equivalent of 500) and 26.8 grams of LG-650 (a polyether triol available from Union Carbide having a OH equivalent of 86.3). The contents were thoroughly mixed and heated toward 80° C., and held at this temperature until the reaction exotherm raised the temperature to about 100° C. The maximum temperature during the reaction was 100° C. Heat was removed, and the mixture was cooled to 80° C. A sample was withdrawn, to determine NCO content. (Percent NCO measured to be 11.8; in theory, 11.6).

This product was further diluted with 212.5 grams of Isonate 240 (an NCO prepolymer available from Upjohn Co.; NCO equivalent weight 225 based primarily on diphenylmethane diisocyanate and diphenylmethane diisocyanate adducts.). The percent of NCO was measured to be 13.0. The ratio of total NCO to total OH equivalents was 4.06:1.00.

The polyurethane prepolymer was catalyzed by the prior art and the claimed invention. To the prepolymer were added a surfactant (optional, Dow Corning 200 fluid or Dow Corning Antifoam A at 0.01 to 0.3 PHR), and the indicated amounts of a stabilizer and a catalyst.

To determine the set time, or cure rate, of the catalyzed resin system, a 4-mil thick resin film of each system was drawn on a clean aluminum surface, and dipped in water (4-mil wet film thickness). A Gardner TM film draw down bar was used to draw the film. The set time was measured at the time of onset of "through cure" of the resin, i.e., a thoroughly polymerized film. The surface cure time, or tack free time, measured the time that takes to form a thin surface film.

To measure viscosity, an indicator of shelf life stability, the compounded neat resins were packaged in aluminum pouches under $N_2$ in a dry box. They were placed in an oven which had been preheated to a constant temperature. The sample was taken out after the given time and allowed to cool to room temperature (75° F.). This cooling was allowed to occur overnight. The viscosity of the equilibrated samples was then measured. As indicated in U.S. Pat. No. 4,433,680, this type of accelerated aging is an excellent indicator of shelf stability, a lower viscosity over any equal amount of time of aging indication superior shelf life. See column 4, lines 37-51.

Figure 2:
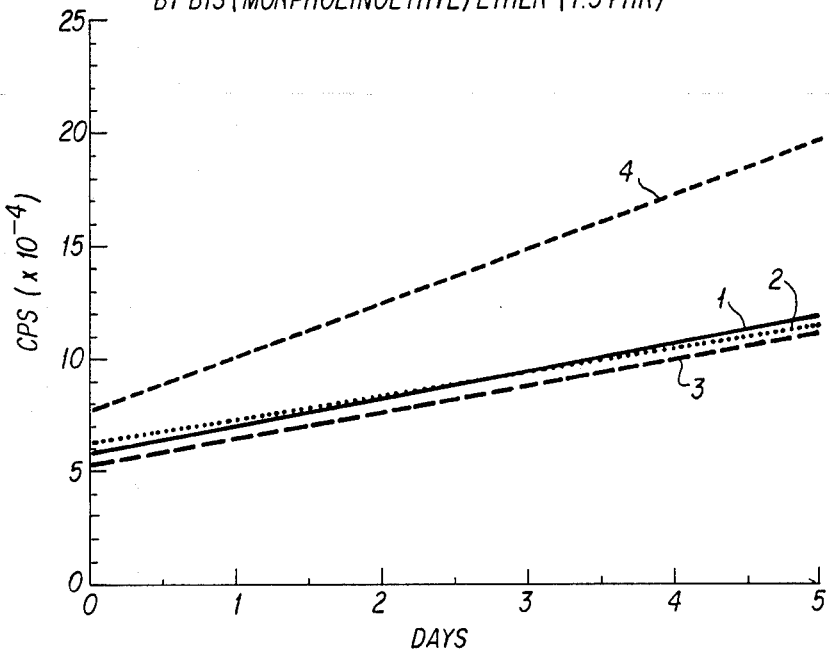
FIG. 2 is a similar graph reflecting systems with a bismorpholinodiethylether catalyst.

The FIG. 1 shows the stabilizing effect of MSA compared with that of benzoyl chloride in Prepolymer A which was catalyzed using the preferred catalyst of U.S. Pat. No. 4,427,002, bis(2-dimethylaminoethyl)ether (A-99 from Union Carbide). FIG. 2 shows the results with the preferred catalyst of U.S. Pat. No. 4,433,680, bismorpholinodiethylether (BMDEE).

One particular application where MSA is particularly desirable as a stabilizing agent, owing to its low toxicity, is in orthopedic casting or splinting materials prepared from carriers or fabrics saturated with catalyzed polyurethane prepolymer system, as indicated above. Among suitable polyurethane prepolymer systems, and carriers saturated with the systems, are those identified in U.S. Pat. Nos. 4,411,262 and 4,427,002. The particular formulation of these polymers is not further addressed herein, and does not constitute part of the invention. In particular, the MSA stabilizer can be substituted for the mineral acid stabilizer of U.S. Pat. No. 4,427,002. Additionally, the MSA out-performs the benzoyl chloride stabilizer of U.S. Pat. No. 4,433,680. Accordingly, one aspect of the invention includes these prior art prepolymers stabilized with appropriate amounts of MSA.

However, even employing MSA as a stabilizer, the necessary cure times cannot be achieved and at the same time maintain satisfactory shelf life or stability for orthopedic applications. Accordingly, it is another aspect of this invention to provide a stabilized, catalyzed system that meets the unique demands of this particular application.

Applicants have discovered that when a polyurethane prepolymer is catalyzed with bis(2,6-dimethylmorpholino)diethylether (hereinafter alternatively referred to as Bis-2,6), shelf is enormously improved, while set or dry times, the time it takes the water-immersed saturated carrier to cure after wrapping about the patient, are as good or better than prior art systems. Use of MSA as a stabilizer in systems catalyzed with the bis(2,6-dimethylmorpholino)diethylether further improves the stability, without sacrificing fast cure times. This is demonstrated by the various systems based on Prepolymer A described above reflected in Table 1.

TABLE 1

The Shelf Life Stability of Catalyzed, Stabilized PREPOLYMER A

| Catalyst | Heat Aged Viscosity in cps, 80° C. days | | | (Preliminary) Cure Rate Tack-Free- Time min. |
|---|---|---|---|---|
| | 2 | 4 | 7 | |
| 1. A-99 (0.175)* | gell | — | — | — |
| 2. A-99; MSA (0.75) (0.035) | 240,000 | 568,000 | — | 1½ |
| 3. A-99; Benzoyl chloride (0.175) (0.10) | — | gell | — | 3 |
| 4. BMDEE (1.50) | — | 236,000 | — | 2 |
| 5. BMDEE; MSA (1.50) (0.035) | — | — | 184,000 | 2½ |
| 6. BMDEE; Benzoyl chloride (1.50) (0.10) | — | — | 312,000 | 2 |
| 7. Bis-2,6 (1.60) | — | 148,000 | — | — |
| 8. Bis-2,6; MSA (1.60) (0.035) | — | — | 176,000 | 2½ |
| 9. Bis-2,6; Benzoyl chloride (1.60) (0.10) | — | — | 290,000 | 2 |

*The numbers in the parenthesis correspond to the amount in PHR.

As reflected in the table, the superior properties of the system employing the particular substituted dimorpholinodiethylether employed herein, quick curing time with extended shelf life, are quite remarkable as compared with the base, unsubstituted compound (BMDEE).

Thus, the catalyzed system of this invention provides a means of greatly extending shelf-life, without sacrificing cure time, regardless of the stabilizer employed (if any). In fact, only a slightly greater amount of the Bis-2,6 catalyst is needed to exhibit *identical* cure times observed with the BMDEE catalyst, about 1.6 PHR vs. 1.5 PHR for the prior art. The shelf life of the system of the invention is indicated to be about 1.5-2 times the prior art.

The Bis-2,6 catalyst employed herein can be prepared by a number of synthesis routes. One method for producing the compound is disclosed in U.S. Pat. No. 4,095,022. Alternatively, bis(2,6-dimethylmorpholino)-diethylether can be prepared by the following reaction pathway:

2(2,6-dimethylmorpholine) + dichlorodiethylether ⟶

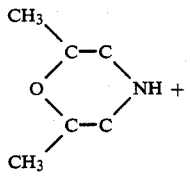

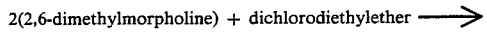

-continued

Cl—CH₂—CH₂—O—CH₂—CH₂—Cl ⟶ bis(2,6-dimethylmorpholinoethyl)ether

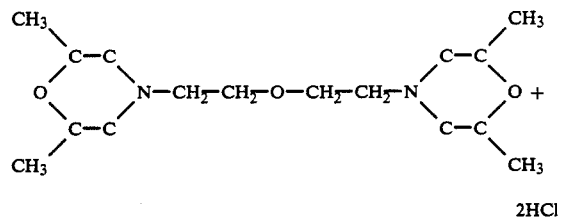

2HCl

To force the reaction to completion, a slight excess of the morpholine compound may be added, such as about 2.4:1.0. A scavenger, such as a TEA (triethylamine) scavenger, may be added to the reaction mixture to trap HCl evolution. The temperature may be taken to the boiling point of the HCl scavenger, with mild refluxing.

The reaction mixture, upon completion of the reaction, divides into a liquid and solid portion. The liquid, when condensed, may be vacuumed distilled, to give purities in excess of 99% of the desired product. A certain amount of the product is lost as a salt, but this salt can be recovered through conventional techniques. Without recovery, yield is 60% theoretical. With recovery, the yield is substantially higher.

The catalyst was also synthesized by the reaction of diethylene glycol and 2,6-dimethylmorpholine.

2 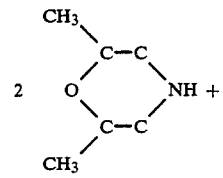

HO—CH₂—CH₂—O—CH₂—CH₂—OH $\xrightarrow{H_2, Pt}$ bis(2,6-dimethylmorpholinoethyl)ether A study of the reaction product indicates that the catalyst contains a mixture of cis and trans substituted morpholine ring structures, as demonstrated by gas chromatography analysis.

The above-described polyurethane prepolymer is a preferred embodiment. Alternative embodiments suitable for use in the invention as an orthopedic casting material are the reaction products described in U.S. Pat. No. 4,411,262. Particularly preferred prepolymers for use in orthopedic casting materials are disclosed in U.S. Pat. No. 4,427,002. Of particular importance are prepolymers based on a diphenylmethane diisocyanate, and a polyol mixture of diols and triols; the diols being selected from the following commercially available compounds: PPG1025 (available from Union Carbide and having a OH No. of 111.4), PPG2025 (also available from Union Carbide and having an OH No. of 56.5), ED1000 (available from Witco, having an OH No. of 111.3), Polyol 24-32 (available from Union Carbide having an OH No. of 32.0); and the triols are selected from the following commercially available products: LG168 (available from Union Carbide having an OH No. of 176.0), LG56 (from Union Carbide, having an OH No. of 57.4), LHT112 (available from Union Carbide, having a OH No. of 114.4), ET700 (availble from Witco and having a OH No. value of 233.6), ET1500 (also available from Witco and having an OH No. of 108.4) and Polyol 34-28 (available from Union Carbide, and having an OH No. of 28.0).

Based on the prepolymer employed, the catalyst should be present in the prepolymer system in amounts of 0.5%–10%. Particularly preferred amounts range from about 1%–5%, by weight of the total mixture.

In addition to its excellent set times, and dramatically improved shelf life, the catalyst employed herein has additional advantages in the particular application of orthopedic casting materials. Due to its lower volatility than prior art catalysts, the catalyst of this invention results in a less objectionable odor, which is important in a hospital or medical field setting. At the same time, the catalyst is markedly less toxic than previously prepared catalysts, a critical consideration whenever health care fields are considered.

The invention herein has been disclosed with reference to particular chemical systems, products and materials. In particular, the universally applicable stabilizer of the invention, methane sulfonic acid has been identified in particular catalyzed, prepolymer systems. These systems should not be taken to be limiting, and the stabilizer has utility in polyurethane systems in general. Accordingly, variations of the specific examples set forth herein will occur to those of ordinary skill in the art without the exercise of inventive faculty.

Similarly, the orthopedic casting material claimed herein has been described with reference to particular prepolymer systems and particular carriers. Substitution of a web or carrier of different materials or construction, as long as the material remains suitable for draping and curing about a limb or other portion of a patient's body to be immobilized, do not take the resulting product outside the scope of this invention. Additionally, other prepolymer systems, which may cure more slowly or more rapidly than those identified herein are suitable for use, provided the set times are not intolerably long. Of course, variations in the amounts included, and methods of production, will occur to those of ordinary skill in the art, without the exercise of inventive faculty. All these variations remain within the scope of the invention, as claimed below.

What is claimed as new and desired to be secured by Letters Patent of the United States is:

1. A polyurethane prepolymer system consisting essentially of an isocyanate-terminated polyurethane prepolymer reaction product of a polyol and a diisocyanate and a tertiary amine catalyst selected from the group consisting of bis(2-dimethylaminoethyl)ether, dimorphilinodiethylether, bis(2,6-dimethylmorpholino) diethylether and mixtures thereof, further consisting essentially of methane sulfonic acid in an amount effective as a shelf life stabilizer therefor.

2. The system of claim 1, wherein said methane sulfonic acid is present in amounts of 0.01–1% by weight.

3. The system of claim 1, wherein said polyol is comprised of a mixture of diols and triols.

4. The system of claim 3, wherein said diols and triols are present in a ratio of 9:1 to 1:9 by equivalents.

5. The system of claim 1, wherein said tertiary amine catalyst is bis(2,6-dimethylmorpholino)diethylether.

6. The system of claim 5, wherein said catalyst is present in amounts of 0.5%–10% by weight of the system.

7. The system of claim 6, wherein said catalyst is present in amounts of 1–5% by weight.

8. A water-curable orthopedic cast bandage which is stable in the absence of water, comprising:
a flexible substrate,
said substrate being coated with a isocyanate terminated polyurethane prepolymer system comprising a polyurethane prepolymer and a catalyst comprising bis(2,6-dimethylmorpholino)diethylether.

9. The orthopedic bandage material of claim 8, wherein said polyurethane system further comprises an effective amount of shelf life stabilizer.

10. The orthopedic bandage material of claim 9, wherein said stabilizer comprises methane sulfonic acid.

11. The orthopedic bandage material of claim 8, wherein said polyurethane prepolymer comprises the reaction product of a diisocyanate and a polyol.

12. The orthopedic bandage material of claim 11, wherein said diisocyanate is comprised of diphenylmethane diisocyanate.

13. The orthopedic bandage material of claim 12, wherein said polyol is comprised of a mixture of diols and triols.

14. The orthopedic bandage material of claim 13, wherein said diols and triols are present in a ratio of 1:9–9:1 by equivalents.

15. A water/curable orthopedic casting material enclosed in a moisture impervious package, which is stable in said package, and may be cured by immersion of said material in water, comprising:
a flexible substrate,
said substrate being coated with an isocyanate terminated polyurethane prepolymer system, comprising a polyurethane prepolymer and a catalyst comprising bis(2,6-dimethylmorpholino)diethylether.

16. The orthopedic casting material of claim 15, wherein said polyurethane system further comprises an effective amount of shelf life stabilizer.

17. The orthopedic bandage material of claim 16, wherein said stabilizer comprises methane sulfonic acid.

18. The orthopedic casting material of claim 15, wherein said polyurethane prepolymer comprises the reaction product of a diisocyanate and a polyol.

19. The orthopedic casting material of claim 18, wherein said diisocyanate is comprised of diphenylmethane diisocyanate.

20. The orthopedic casting material of claim 19, wherein said polyol is comprised of a mixture of diols and triols.

21. The orthopedic casting material of claim 20, wherein said diols and triols are present in a ratio of 1:9–9:1 by equivalents.

* * * * *